United States Patent
Ito et al.

(10) Patent No.: US 8,349,597 B2
(45) Date of Patent: Jan. 8, 2013

(54) LACTIC ACID PRODUCTION METHOD

(75) Inventors: Masateru Ito, Kanagawa (JP); Shin-ichi Minegishi, Shiga (JP); Eri Shimizu, Shiga (JP); Kenji Sawai, Kanagawa (JP); Yohito Ito, Shiga (JP); Hideki Sawai, Kanagawa (JP); Katsushige Yamada, Kanagawa (JP)

(73) Assignee: Toray Industries, Inc. (JP)

( * ) Notice: Subject to any disclaimer, the term of this patent is extended or adjusted under 35 U.S.C. 154(b) by 315 days.

(21) Appl. No.: 12/666,690

(22) PCT Filed: Jun. 18, 2008

(86) PCT No.: PCT/JP2008/061105
§ 371 (c)(1), (2), (4) Date: Jan. 11, 2010

(87) PCT Pub. No.: WO2009/004922
PCT Pub. Date: Jan. 8, 2009

(65) Prior Publication Data
US 2010/0190222 A1    Jul. 29, 2010

(30) Foreign Application Priority Data

Jun. 29, 2007 (JP) ................ 2007-172082
Jul. 31, 2007 (JP) ................ 2007-198567

(51) Int. Cl.
*C12P 7/56* (2006.01)
(52) U.S. Cl. .............. 435/139; 435/135; 562/589
(58) Field of Classification Search ............ 435/135, 435/139; 562/589
See application file for complete search history.

(56) References Cited

U.S. PATENT DOCUMENTS

| | | | |
|---|---|---|---|
| 3,262,862 A * | 7/1966 | Kitahara | ............ 435/139 |
| 4,758,343 A | 7/1988 | Sasaki et al. | |
| 5,250,182 A | 10/1993 | Bento et al. | |
| 5,503,750 A | 4/1996 | Russo, Jr. et al. | |
| 5,681,728 A | 10/1997 | Miao | |
| 6,221,225 B1 | 4/2001 | Mani | |
| 6,489,508 B1 | 12/2002 | Van Gansbeghe et al. | |
| 2003/0125581 A1 * | 7/2003 | Gerkema et al. | ............ 562/589 |
| 2004/0033573 A1 | 2/2004 | Norddahl et al. | |

FOREIGN PATENT DOCUMENTS

| | | |
|---|---|---|
| DE | 195 80 599 C1 | 2/1999 |
| JP | 62-72646 A | 4/1987 |
| JP | 62-201606 A | 9/1987 |
| JP | 6-306011 A | 11/1994 |
| JP | 2001-506274 A | 5/2001 |
| JP | 2005-270025 | 10/2005 |
| WO | 95/33696 | 12/1995 |
| WO | 01/25180 A1 | 4/2001 |

OTHER PUBLICATIONS

Kotz et al. "Chemistry and Chemical Reactivity" 2nd edition (1991) (Saunder College Publishing: Ft. Worth) p. 339.*
Timmer, J.M.K. et al., "Lactic Acid Separation from Fermentation Broths by Reverse Osmosis and Nanofiltration," *Journal of Membrane Science*, 1994, vol. 92, pp. 185-197.

* cited by examiner

*Primary Examiner* — Susan Hanley
(74) *Attorney, Agent, or Firm* — DLA Piper LLP (US)

(57) ABSTRACT

A method of producing lactic acid by separating lactic acid produced in a culture solution by microbial fermentation, comprising: a step (A) of filtering the culture solution through a nano-filtration membrane; and a step (B) of distilling a lactic-acid-containing solution produced in step (A) under a pressure of 1 Pa to atmospheric pressure at a temperature of 25 to 200° C. to recover lactic acid.

7 Claims, 1 Drawing Sheet

SEQUENCE LISTING

```
<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctcgagatgg caactctaaa ggatca                                          26

<210> SEQ ID NO 2
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 2
gcggccgctt aaaattgcag ctcctttt                                            28

<210> SEQ ID NO 3
<211> LENGTH: 999
<212> TYPE: DNA
<213> ORGANISM: Homo sapiens

<400> SEQUENCE: 3
atggcaactc taaaggatca gctgatttat aatcttctaa aggaagaaca gaccccccag          60
aataagatta cagttgttgg ggttggtgct gttggcatgg cctgtgccat cagtatctta         120
atgaaggact tggcagatga acttgctctt gttgatgtca tcgaagacaa attgaaggga         180
gagatgatgg atctccaaca tggcagcctt ttccttagaa caccaaagat tgtctctggc         240
aaagactata atgtaactgc aaactccaag ctggtcatta tcacggctgg ggcacgtcag         300
caagagggag aaagccgtct taatttggtc agcgtaacg tgaacatatt taaattcatc          360
attcctaatg ttgtaaaata cagcccgaac tgcaagttgc ttattgtttc aaatccagtg         420
gatatcttga cctacgtggc ttggaagata agtggttttc ccaaaaaccg tgttattgga         480
agtggttgca atctggattc agcccgattc cgttacctga tgggggaaag gctgggagtt         540
cacccattaa gctgtcatgg gtgggtcctt ggggaacatg gagattccag tgtgcctgta         600
tggagtggaa tgaatgttgc tggtgtctct ctgaagactc tgcacccaga tttagggact         660
gataaagata aggaacagtg gaaagaggtt cacaagcagg tggttgagag tgcttatgag         720
gtgatcaaac tcaaaggcta cacatcctgg gctattggac tctctgtagc agatttggca         780
gagagtataa tgaagaatct taggcgggtg cacccagttt ccaccatgat taagggtctt         840
tacggaataa aggatgatgt cttccttagt gttccttgca ttttgggaca gaatggaatc         900
tcagaccttg tgaaggtgac tctgacttct gaggaagagg cccgtttgaa gaagagtgca         960
gatacacttt gggggatcca aaaggagctg caatttttaa                               999

<210> SEQ ID NO 4
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctcaattat tattttctac tcataacctc acgcaaaata acacagtcaa atcaatcaaa          60
atggcaactc taaaggatca                                                     80

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggcgtatca cgaggccctt                                                     20
```

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaattaattc ttgaagacga aagggcctcg tgatacgcct agattgtact gagagtgcac    60

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tatttttcgt tacataaaaa tgcttataaa actttaacta ataattagag attaaatcgc    60
ctgtgcggta tttcacaccg                                                80

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caaatatcgt ttgaatattt ttccg                                          25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aatccagatt gcaaccactt                                                20

LACTIC ACID PRODUCTION METHOD

RELATED APPLICATIONS

This is a §371 of International Application No. PCT/JP2008/061105, with an international filing date of Jun. 18, 2008 (WO 2009/004922 A1, published Jan. 8, 2009), which is based on Japanese Patent Application Nos. 2007-172082, filed Jun. 29, 2007, and 2007-198567, filed Jul. 31, 2007, the subject matter of which is incorporated by reference.

SEQUENCE LISTING

This application contains a Sequence Listing which has been submitted via EFS-Web and is hereby incorporated by reference in its entirety. The ASCII copy, created on Feb. 24, 2010, is named TOR09131.txt, and is 3,821 bytes in size.

TECHNICAL FIELD

This disclosure relates to a method of producing lactic acid by separating lactic acid produced in a culture solution by microbial fermentation. Specifically, it relates to a method of producing lactic acid by removing an inorganic salt remained in a microorganism culture solution through a nano-filtration membrane and distilling the resultant lactic acid-containing solution.

BACKGROUND

Lactic acid is widely applied even in an industrial use as a monomer raw material of biodegradable plastics other than a use for food, medicine and the like, and the demand is increasing. It is known that 2-hydroxypropionic acid, i.e., lactic acid is produced by a microbial fermentation, and the microorganism converts a substrate containing carbohydrate typified by glucose into lactic acid. Lactic acid is classified into optical isomers of (L)-isomer and (D)-isomer based on the configuration of a hydroxyl group bonded to a carbonyl carbon of α-position. Microbial fermentation can produce lactic acid of (L)-isomer or (D)-isomer selectively, or of a mixture (racemic body) of (L)-isomer and (D)-isomer by suitably choosing a microorganism.

The production of lactic acid by microbial fermentation is generally conducted while being maintained at an optimum pH for microbial fermentation by adding an alkaline substance to a culture solution. Lactic acid, an acidic substance produced by microbial fermentation, is mostly present as lactate in a culture solution by being added with an alkaline substance. In this case, free lactic acid is obtained by adding an acidic substance to a culture solution after completion of fermentation. Specifically, as one example of the alkaline substance to be added to a culture solution, calcium hydroxide is used, in this case, lactic acid produced by microbial fermentation is present as calcium lactate in a culture solution. Thereafter, by adding an acidic substance (for example, sulfuric acid) to a culture solution after completion of culture, a solution of free lactic acid can be obtained, but a calcium salt (for example, calcium sulfate) is produced as a by-product.

As a method for separating lactic acid by removing the calcium salt produced, in the case that a calcium salt is a poorly-soluble and precipitates like calcium sulfate, a method of filtering out through qualitative filter paper or the like is used. However, in the case of this method, a calcium salt that precipitates as a solid is removed, but a small amount of calcium salt dissolved in a solution is not removed, thus, it will remain in a lactic acid-containing solution. In the case that lactic acid is produced by microbial fermentation, various inorganic salts other than target lactic acid are produced as by-products, of which ones dissolved in a culture solution cannot be filtered out through qualitative filter paper or the like. Therefore, for example, when this filtrate containing lactic acid is subjected to a concentration procedure in the subsequent purification process, there arises a problem that calcium salt and other inorganic salts separate out (precipitation) again in a solution containing free lactic acid. When a lactic acid-containing solution is heated in operations such as distillation in a state that inorganic ions are not sufficiently removed, it is known that racemization and oligomerization of lactic acid proceed by the influence of inorganic ions. Therefore, a method for effectively removing a small amount of inorganic ion components remained in a lactic acid-containing solution is desirable.

As a method for removing a small amount of inorganic ion components from a lactic acid-containing solution, a method using an ion-exchange resin is disclosed (for example, see Japanese translation of PCT Publication No. 2001-506274). However, for maintaining ion-exchange performance of an ion-exchange resin, it is necessary to regenerate the ion-exchange resin periodically. In such regeneration of the ion-exchange resin, it is carried out using a large amount of sodium chloride aqueous solution, there is a problem that a lot of waste liquid is discharged being accompanied with regeneration, so that waste liquid treatment costs a lot. Further, there has been a problem that when an ion-exchange resin is regenerated repeatedly, the regeneration rate of an ion-exchange resin is lowered, in addition thereto, the ion-exchange performance is lowered, and the removal rate of inorganic salts is lowered.

There is also the known method that a small amount of inorganic ion components such as calcium component is removed from a lactic acid-containing solution by a bipolar membrane using an electrodialyzer (for example, see Japanese Unexamined Patent Publication No. 2005-270025). However, there has been a problem that the bipolar membrane used in this method is expensive, in addition thereto, the removal efficiency of inorganic salts such as calcium salt is by no means high.

In addition, a method of separation and recovery of organic acid using a separation membrane is known, and a method of separating para-pyruvic acid from a pyruvic acid solution through a reverse osmosis membrane is disclosed (see Japanese Unexamined Patent Publication No. 6-306011), but in that case, the removal rate of inorganic salts is not disclosed. Japanese Unexamined Patent Publication No. 6-306011 relates to a method of separation and recovery of pyruvic acid, but since pyruvic acid is not an optically-active material, problems in separation and recovery of lactic acid from a lactic acid-containing solution, namely, racemization and oligomerization have not been solved yet.

Further, a method of removing inorganic salts from a lactic acid-containing solution using a nano-filtration membrane is disclosed (for example, see U.S. Pat. No. 5,503,750, U.S. Pat. No. 5,681,728 and US 2004/0033573), but there is no disclosure on a process for recovery of lactic acid by distilling a lactic acid-containing solution obtained by filtrating a fermentation culture solution of a microorganism through a nano-filtration membrane, and on the influence that distillation affects the yield of lactic acid, so that the object of recovering lactic acid in a high yield by distillation has not been solved.

It could therefore be helpful to provide a method of effectively separating and recovering lactic acid in a culture solution while suppressing racemization and oligomerization.

SUMMARY

We found that by distilling a lactic acid-containing solution obtained by filtering a microbial fermentation culture solution containing lactic acid using a nano-filtration membrane, lactic acid can be efficiently separated and recovered while suppressing racemization of lactic acid, and have completed this disclosure.

We thus provide the following (1) to (9):

(1) A method of producing lactic acid, which is a method of producing lactic acid by separating lactic acid produced in a culture solution by means of microbial fermentation, comprising: a step A of filtering the culture solution through a nano-filtration membrane; and a step B of distilling a lactic acid-containing solution obtained in the step A under a pressure ranging from 1 Pa to an atmospheric pressure (inclusive) at a temperature ranging from 25° C. to 200° C. (inclusive) to recover lactic acid.

(2) The method of producing lactic acid described in (1), wherein pH of the culture solution to be filtrated through the nano-filtration membrane in said step A is not less than 2 and not more than 4.5.

(3) The method of producing lactic acid described in (1) or (2), wherein the culture solution is a culture solution by the microbial fermentation in the presence of calcium salt, a culture solution containing lactic acid obtained after a step C of removing a calcium component in said culture solution as a poorly-soluble sulfate salt is provided to said step A.

(4) The method of producing lactic acid described in any one of (1) to (3), wherein the ratio of permeability of magnesium sulfate to permeability of citric acid through the nano-filtration membrane is 3 or more at 0.5 MPa of operation pressure, 25° C. of raw water temperature, and 1000 ppm of raw water concentration.

(5) The method of producing lactic acid described in any one of (1) to (4), wherein the permeability of magnesium sulfate through the nano-filtration membrane is 1.5% or less at 0.5 MPa of operation pressure, 25° C. of raw water temperature, and 1000 ppm of raw water concentration.

(6) The method of producing lactic acid described in any one of (1) to (5), wherein a membrane material of the nano-filtration membrane includes polyamide.

(7) The method of producing lactic acid described in (6), wherein the polyamide is composed of crosslinked piperazine polyamide as a main component, and contains a constitutional component shown in a chemical formula (1):

STR (1)

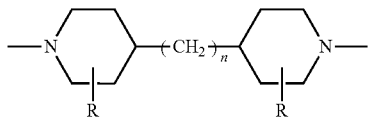

Chemical formula (1)

wherein R represents —H or —CH$_3$, and n represents an integer from 0 to 3 (inclusive).

(8) The method of producing lactic acid described in any one of (1) to (7), wherein the filtration pressure of the culture solution in step A is not less than 0.1 MPa and not more than 8 MPa.

(9) The method of producing lactic acid described in any one of (1) to (8), comprising a step D of increasing the concentration of lactic acid by filtering a lactic acid-containing solution obtained in step A through a reverse osmosis membrane.

An inorganic salt dissolved in a fermentation culture solution or contained therein as a poorly-soluble solid is effectively removed by a simple operation, and racemization and oligomerization of lactic acid during the production process are suppressed, thus lactic acid can be produced in high purity and a high yield.

DESCRIPTION OF NUMBERS AND SYMBOLS

Figure 1:
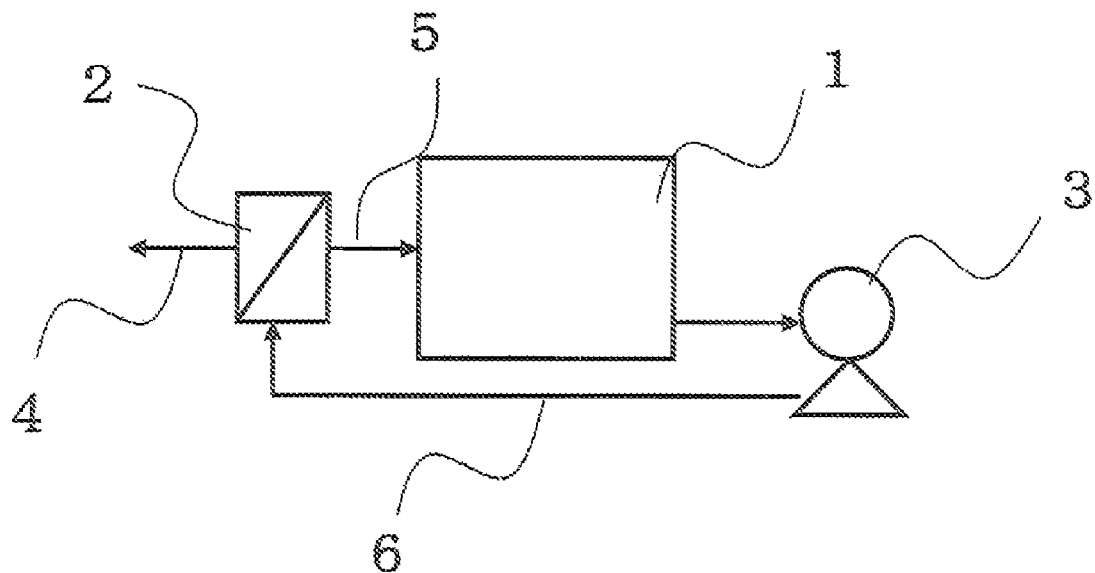
FIG. 1 is a schematic diagram showing one example of a nano-filtration membrane separator.

1 Raw water tank
2 Cell equipped with nano-filtration membrane or reverse osmosis membrane
3 High-pressure pump
4 Flow of membrane-permeated liquid
5 Flow of membrane-concentrated liquid
6 Flow of culture solution sent by high-pressure pump
7 Nano-filtration membrane
8 Supporting plate

DETAILED DESCRIPTION

The method of producing lactic acid is a method of producing lactic acid by separating lactic acid produced in a culture solution by means of microbial fermentation, and it includes a step A of filtering the fermentation culture solution through a nano-filtration membrane to remove an inorganic salt in the fermentation culture solution for obtaining a lactic acid solution; and a step B of distilling a lactic acid-containing solution obtained in the step A under a pressure ranging from 1 Pa to an atmospheric pressure (inclusive) at a temperature ranging from 25° C. to 200° C. (inclusive) to recover lactic acid.

A nano-filtration membrane used in the step A is also called a nano-filter (nano-filtration membrane, NF membrane), and is a membrane generally defined as "membrane permeating a monovalent ion but preventing a divalent ion." It is a membrane probably having a fine pore of about several nanometers, and it is mainly used to prevent fine particles, molecules, ions, salts and the like in water.

"Filtering through a nano-filtration membrane" means that a culture solution containing lactic acid produced by microbial fermentation is filtered through a nano-filtration membrane; an inorganic salt dissolved or deposited as a solid is removed, prevented or filtered out to permeate a lactic acid solution as filtrate. Herein, an inorganic salt includes any form of inorganic salt contained in a culture solution, which includes any one contained in a state dissolved in a culture solution, or deposited or precipitated in a culture solution.

It is preferable that pH of a culture solution to be supplied to a nano-filtration membrane in the step A is not less than 2.0 and not more than 4.5. Since it is known that a nano-filtration membrane removes or prevents a substance ionized in a solution more easily than one not ionized, by setting pH of a culture solution to be 4.5 or less, the ratio that lactic acid is dissociated in a culture solution and present as a lactic acid ion is lowered, and lactic acid can be permeated easily. When pH is less than 2.0, it may damage the nano-filtration membrane. Further, pKa of lactic acid is 3.86, so that when pH is set to be 3.86 or less, lactic acid not dissociated into a lactic acid ion and hydrogen ion is more contained in a culture solution, hence lactic acid can be efficiently permeated through a nano-filtration membrane, which is more preferable. Additionally, the adjustment of pH of a culture solution may be done during or after microbial fermentation.

As a culture solution to be supplied to a nano-filtration membrane in the step A, it is preferable to use a culture solution obtained by maintaining an optimum pH for microbial fermentation by adding an alkaline substance to a culture solution. The alkaline substance to be added is not particularly limited, and it is preferable to add a basic calcium salt. By adding a basic calcium salt to a culture solution, it becomes possible to introduce a step C of removing a calcium component in a culture solution as a poorly-soluble sulfate salt in the previous step of step A. Specifically, for example, the step C where sulfuric acid is added to a culture solution to precipitate and filter out a calcium component in a culture solution as calcium sulfate being a poorly-soluble sulfate salt is conducted, and by filtrating the filtrate (separated liquid containing lactic acid) through a nano-filtration membrane of step A, it becomes possible to remove or prevent a calcium component more effectively. As the basic calcium salt, there are listed calcium hydroxide, calcium carbonate, calcium phosphate, calcium oxide, calcium acetate and the like, and calcium hydroxide is preferable. In the case that a calcium component in a culture solution is precipitated and filtered out as a poorly-soluble sulfate salt, when the equivalent of sulfuric acid to be added into a culture solution exceeds the equivalent of calcium (sulfuric acid equivalent>calcium equivalent), the excess amount of sulfuric acid is permeated partly through a nano-filtration membrane, thereafter, when the permeate is heated such as during concentration and distillation, the sulfuric acid permeated may work as a catalyst of promoting oligomerization of lactic acid to lower distillation yield. Hence, in the case that a calcium component in a culture solution is precipitated and filtered out as a poorly-soluble sulfate salt, it is preferable to add sulfuric acid by the amount of not more than the equivalent of a calcium component in a culture solution, and in the case of adjusting the equivalent of addition by pH, pH of 2.0 or more is preferable because of being not more than the equivalent of calcium component.

As a method for evaluating the level of removal, prevention or filtering out of inorganic salts dissolved or deposited as a solid for a nano-filtration membrane used in the present invention, a method of evaluation by calculating a removal rate (rejection) of inorganic ions is mentioned, but it is not limited to this method. The rejection (removal rate) of inorganic salts can be calculated according to a formula 1, by measuring the concentration of inorganic salts contained in a raw water (culture solution) (raw water inorganic salt concentration) and the concentration of inorganic salts contained in a permeated liquid (lactic acid solution) (permeated liquid inorganic salt concentration) based on an analysis typified by an ion chromatography.

$$\text{Inorganic salt-removal rate}(\%) = (1-(\text{permeated liquid inorganic salt concentration/raw water inorganic salt concentration})) \times 100 \quad \text{(Formula 1)}$$

The performance of membrane separation of a nano-filtration membrane used in the step A is not particularly limited, and preferably used is the one that the ratio of permeability of magnesium sulfate to permeability of citric acid through a nano-filtration membrane is 3 or more at 0.5 MPa of operation pressure, 25° C. of raw water temperature, and 1000 ppm of raw water concentration. When the ratio of permeability of magnesium sulfate to permeability of citric acid through a nano-filtration membrane is 3 or more in the above-described condition, it is preferable because an inorganic salt contained in a culture solution is removed and lactic acid can be permeated efficiently. Here, the permeability of magnesium sulfate can be calculated according to a formula 2, by measuring the concentration of magnesium sulfate contained in a raw water (raw water magnesium sulfate concentration) and the concentration of magnesium sulfate contained in a permeated liquid (permeated liquid magnesium sulfate concentration) based on an analysis typified by an ion chromatography. Similarly, as for the permeability of citric acid, it can be calculated by replacing concentration of citric acid for concentration of magnesium sulfate in the formula 2, by measuring the concentration of citric acid contained in a raw water (raw water citric acid concentration) and the concentration of citric acid contained in a permeated liquid (permeated liquid citric acid concentration) based on an analysis typified by a high-performance liquid chromatography.

$$\text{Magnesium sulfate permeability}(\%) = (\text{permeated liquid magnesium sulfate concentration})/(\text{raw water magnesium sulfate concentration}) \times 100 \quad \text{(Formula 2)}$$

Preferably used is the one that the permeability of magnesium sulfate is 1.5% or less at 0.5 MPa of operation pressure, 25° C. of raw water temperature, and 1000 ppm of raw water concentration. In the case that the permeability of magnesium sulfate through a nano-filtration membrane exceeds 1.5% in the above-described condition, inorganic salts may be deposited when the lactic acid solution permeated through a nano-filtration membrane is concentrated, further, when distillation operation is conducted, racemization and oligomerization of lactic acid tend to occur by the influence of inorganic salts permeated, and it may lower distillation yield. More preferably, the one that the permeability of magnesium sulfate through a nano-filtration membrane is 1.0% or less is used.

In addition, a nano-filtration membrane of 45% or more in the removal rate of sodium chloride (500 mg/L) is preferably used. As the permeation performance of nano-filtration membrane, a nano-filtration membrane that permeation flow volume ($m^3/m^2/day$) of sodium chloride (500 mg/L) per unit area of membrane at a filtration pressure of 0.3 MPa is not less than 0.5 and not more than 0.8 is preferably used. As an evaluation method of permeation flow volume per unit area of membrane (membrane permeation flux), it can be calculated according to a formula 3 by measuring the amount of permeated liquid, time for sampling the amount of permeated liquid, and membrane area.

$$\text{Membrane permeation flux}(m^3/m^2/day) = \text{Amount of permeated liquid/Membrane area/Sampling time} \quad \text{(Formula 3)}$$

For a material of the nano-filtration membrane, polymer materials such as cellulose acetate polymers, polyamide, polyester, polyimide and vinyl polymer can be used, but it is not limited to a membrane composed of one kind of the foregoing material, and it can also be a membrane of composite membrane materials. The membrane structure may be either an asymmetric membrane which has a dense layer to at least one surface of a membrane and has fine pores with a gradually increasing pore diameter inside the membrane or toward the other surface from the dense layer; or a composite membrane which has a very thin functional layer formed by other material on the dense layer of an asymmetric membrane. As the composite membrane, for example, a membrane constructed from a polysulfone supporting membrane material and a polyamide nano-filter functional layer described in Japanese Unexamined Patent Publication No. 62-201606 can be used.

Among these, it is preferable to use a composite membrane composed of polyamide as a functional layer which has the excellent potentials of having high pressure resistance, high water-permeability and high solute-removable performance all together. For maintaining durability against operation pressure, high water-permeability and prevention performance, one with a structure where polyamide is a functional layer which is held with a support composed of porous film or non-woven cloth is suitable. As a polyamide semipermeable membrane, it is suitable to use a composite semipermeable membrane where a functional layer of crosslinked polyamide obtained by polycondensation reaction of multifunctional amine with multifunctional halide is present on a supporting material.

As a preferable carboxylic acid component of a monomer composing polyamide as the functional layer in a nano-filtration membrane, there are listed aromatic carboxylic acids such as trimesic acid, benzophenone tetracarboxylic acid, trimellitic acid, pyromellitic acid, isophthalic acid, terephthalic acid, naphthalene dicarboxylic acid, diphenylcarboxylic acid and pyridinecarboxylic acid. However, in consideration of the solubility in a solvent for film production, trimesic acid, isophthalic acid, terephthalic acid, and a mixture thereof are more preferable.

As a preferable amine component of a monomer composing the above-described polyamide, there are listed primary diamines with an aromatic ring such as m-phenylenediamine, p-phenylenediamine, benzidine, methylenebisdianiline, 4,4'-diaminobi-phenylether, dianisidine, 3,3',4-triaminobiphenylether, 3,3',4,4'-tetraminobiphenylether, 3,3'-dioxybenzidine, 1,8-naphthalenediamine, m(p)-monomethylphenylenediamine, 3,3'-mono-methylamino-4,4'-diaminobiphenylether, 4,N,N'-(4-aminobenzoyl)-p(m)-phenylenediamine-2,2'-bis(4-aminophenylbenzoimidazole), 2,2'-bis(4-aminophenylbenzooxazole) and 2,2'-bis(4-aminophenylbenzothiazole); and secondary diamines such as piperazine, piperidine, or derivatives thereof. Above all, a nano-filtration membrane that contains piperazine or piperidine as a monomer of the crosslinked polyamide functional layer is preferably used because of having heat resistance and chemical resistance as well as pressure resistance and durability. More preferable is polyamide consisting of the foregoing crosslinked piperazine polyamide or crosslinked piperidine polyamide as a main component, and containing the constitutional component shown in the above-described chemical formula (1), further preferable is polyamide consisting of the crosslinked piperazine polyamide as a main component, and containing the constitutional component shown in the above-described chemical formula (1). One with n=3 in the above-described chemical formula (1) is preferably used. As the nano-filtration membrane with polyamide consisting of the crosslinked piperazine polyamide as a main component and containing the constitutional component shown in the above-described chemical formula (1) as a functional layer, for example, one described in Japanese Unexamined Patent Publication No. 62-201606 is listed, as the specific example, there is listed UTC60 of a crosslinked piperazine polyamide-based semipermeable membrane manufactured by Toray Industries, Inc., whose functional layer is polyamide consisting of the crosslinked piperazine polyamide as a main component and containing one with n=3 in the above-described chemical formula (1) as the constitutional component.

A nano-filtration membrane is generally used as a membrane element of spiral form, a nano-filtration membrane used in the present invention is also preferably used as a membrane element of spiral form. As the specific example of a preferable nano-filtration membrane element, for example, there are listed GEsepa of a nano-filtration membrane being a cellulose acetate-based nano-filtration membrane, manufactured by GE Osmonics Corporation; NF99 or NF99HF of a nano-filtration membrane with polyamide as a functional layer, manufactured by Alfa-Laval Corporation; NF-45, NF-90, NF-200 or NF-400 of a nano-filtration membrane with crosslinked piperazine polyamide as a functional layer manufactured by Filmtec Corporation; or SU-210, SU-220, SU-600 or SU-610 of a nano-filtration membrane module manufactured by Toray Industries, Inc, including UTC60 composed of polyamide which has crosslinked piperazine polyamide as a main component and contains the constitutional component shown in the above-described chemical formula (1) as a functional layer, manufactured by Toray Industries, Inc.; and more preferably, NF99 or NF99HF of a nano-filtration membrane with polyamide as a functional layer, manufactured by Alfa-Laval; NF-45, NF-90, NF-200 or NF-400 of a nano-filtration membrane with crosslinked piperazine polyamide as a functional layer manufactured by Filmtec Corporation; or SU-210, SU-220, SU-600 or SU-610 of a nano-filtration membrane module manufactured by Toray Industries, Inc., including UTC60 composed of polyamide which has crosslinked piperazine polyamide as a main component and contains the constitutional component shown in the above-described chemical formula (1) as a functional layer, manufactured by Toray Industries, Inc.; and further preferably SU-210, SU-220, SU-600 or SU-610 of a nano-filtration membrane module manufactured by Toray Industries, Inc., including UTC60 composed of polyamide which has crosslinked piperazine polyamide as a main component and contains the constitutional component shown in the above-described chemical formula (1) as a functional layer, manufactured by Toray Industries, Inc.

The filtration of a microbial fermentation culture solution through a nano-filtration membrane in the step A may be done by applying a pressure, the filtration pressure is used preferably in a range from 0.1 Ma to 8 MPa (inclusive). When filtration pressure is less than 0.1 MPa, membrane permeation rate decreases, and when it is more than 8 MPa, it may damage the membrane. It is more preferable when the filtration pressure used is from 0.5 MPa to 7 MPa (inclusive), because a lactic acid solution can be permeated efficiently because membrane permeation flux is high, and because there is less possibility to inflict damage on the membrane, and usage from 1 MPa to 6 MPa (inclusive) is particularly preferable.

The concentration of lactic acid in a microbial fermentation culture solution to be filtered through a nano-filtration membrane of step A is not particularly limited, and being high concentration is suitable because concentration of lactic acid contained in a permeated liquid is also high, so that time for concentration can be shortened to save costs.

The concentration of an inorganic salt contained in a culture solution in the step A is not particularly limited, and it may be equal to or higher than saturated solubility. Namely, when an inorganic salt is in its saturation solubility or less, it is dissolved in a culture solution, and when it is above its saturation solubility, a part thereof is deposited, and since the method for producing lactic acid of the present invention can remove or prevent any one contained in a state dissolved in a culture solution, and deposited or precipitated in a culture solution, filtration of lactic acid can be conducted regardless of the inorganic salt concentration.

As an evaluation method of permeation property of lactic acid through a nano-filtration membrane in separation of lactic acid from a culture solution by the above-described method, it can be evaluated by calculating lactic acid permeability. Lactic acid permeability can be calculated according to a formula 4 by measuring lactic acid concentration contained in a raw water (culture solution) (raw water lactic acid concentration), and lactic acid concentration contained in a permeated liquid (lactic acid-containing solution) (permeated liquid lactic acid concentration) based on an analysis typified by a high-performance liquid chromatography.

Lactic acid permeability(%)=(permeated liquid lactic acid concentration/raw water lactic acid concentration)×100    (Formula 4)

The method of producing lactic acid is characterized in that a lactic acid-containing solution obtained by filtering a culture solution through a nano-filtration membrane of step A is further supplied to a step B of distillation, thereby to obtain lactic acid of high purity. The distillation step is conducted under a reduced pressure ranging from 1 Pa to an atmospheric pressure (normal pressure, about 101 kPa) (inclusive). It is more preferable to conduct distillation under a reduced pressure from 10 Pa to 30 kPa (inclusive), because distillation temperature can be decreased. Regarding the distillation temperature conducted under reduced pressures, it is conducted at a temperature ranging from 20° C. to 200° C. (inclusive), when distillation is conducted at 180° C. or more, there is a possibility that lactic acid might be racemized by the influence of impurities, thus, distillation of lactic acid can be suitably conducted from 50° C. to 180° C. (inclusive), more preferably from 60° C. to 150° C. (inclusive).

Before being supplied to the above-described step B, a lactic acid-containing solution permeated through a nano-filtration membrane may be once concentrated using a concentration apparatus typified by an evaporator, or a lactic acid-containing solution obtained in the step A may be further supplied to a step D of increasing lactic acid concentration by filtering trough a reverse osmosis membrane, but from a viewpoint of energy reduction for concentration, the step D of increasing lactic acid concentration by filtering through a reverse osmosis membrane can be preferably adopted. Herein, a reverse osmosis membrane is a filtration membrane for removing ions and low molecular weight molecules by a driving force caused by pressure difference over the osmotic pressure of water to be treated, for example, there can be adopted cellulosic one such as cellulose acetate, a membrane where a multifunctional amine compound and a multifunctional acid halide are polycondensated to dispose a polyamide separating-functional layer on a microporous supporting membrane, and the like. For suppressing dirt or fouling on the surface of a reverse osmosis membrane, there can also be preferably adopted a low-fouling reverse osmosis membrane mainly for sewage treatment where an aqueous solution of a compound having at least one reactive group to react with an acid halide group is coated on the surface of a polyamide separating-functional layer, and a covalent bond is formed between an acid halide group remained on the surface of the separating-functional layer and the reactive group. Since almost all part of divalent calcium ions were removed in the step A, a stable membrane-concentration can be carried out while producing no scale on the surface of a reverse osmosis membrane.

Next, production of lactic acid by microbial fermentation to be provided to the method for producing lactic acid is explained.

As a raw material used in the production of lactic acid by means of a microbial fermentation, any can be used as long as it promotes the growth of the microorganism cultured to well produces lactic acid as the target fermentation product, and an ordinary liquid culture medium is good, suitably containing a carbon source, a nitrogen source, inorganic salts, and organic trace nutrients such as amino acid and vitamin according to need. As the carbon source, there are used sugars such as glucose, sucrose, fructose, galactose and lactose, saccharified starch solution containing these sugars, sweet potato molasses, sugar beat molasses, high-test molasses, further, organic acids such as acetic acid, alcohols such as ethanol, glycerin and the like. As the nitrogen source, there are ammonia gas, aqueous ammonia, ammonium salts, urea, nitrates; and other organic nitrogen source used secondarily, for example, oilcakes, soybean hydrolysate, casein digest, other amino acid, vitamins, corn steep liquor, yeast or yeast extract, meat extract, peptides such as peptone, various kinds of fermentation fungi and their hydrolysates. As the inorganic salts, phosphate, magnesium salt, calcium salt, iron salt, manganese salt and the like can be suitably added. In the case that a specific nutrient (for example, amino acid, etc.) is needed for growth of a microorganism used in the present invention, the nutrient itself or a natural product containing it is added. A defoaming agent may be used if necessary. A culture solution means a liquid obtained by the result of proliferation of a microorganism or culture cell in a raw material for fermentation. Composition of fermentation raw materials added to a culture solution may suitably be changed from the composition of fermentation raw material at the beginning of culture in order to enhance the productivity of target lactic acid.

A culture of a microorganism is preferably in a range of pH 4 to 8 and temperature 20 to 40° C. When higher oxygen supply rate is required in the culture of microorganism, actions such as maintaining oxygen concentration at 21% or more by adding oxygen to air, pressurizing culture, increasing stirring speed, or increasing airflow rate can be done.

In the early stage of the microorganism culture, a continuous culture (pulling-out) may be started after increasing the microorganism concentration by conducting Batch culture or Fed-Batch culture, or a continuous culture may be conducted at the same time as the start of the culture by innoculating microorganism in high concentration. It is possible to conduct the supply of raw material culture solution and pulling-out of cultured material after a suitable period of time. The starting time of the supply of raw material culture solution and the pulling-out of cultured material is not necessarily the same. The supply of raw material culture solution and pulling-out of cultured material may be continuous or intermittent. Foregoing nutrients necessary for the growth of microorganism may be added to the raw material culture solution so that the growth of microorganism is conducted continuously. In order to obtain an efficient productivity, the concentration of microorganism or culture cell in the culture solution is maintained preferably in a high condition within a range not permitting that the environment of the culture solution becomes unsuitable for the growth of a microorganism or culture cell and the perishing ratio becomes high, for example, a good production efficiency is obtained by maintaining at 5 g/L or more as a dry weight.

A continuous culture operation while growing fresh microorganism having a fermentation ability is ordinarily conducted preferably in a single fermentation tank from a point of culture control. However, the number of fermentation tanks is not concerned as long as it is a continuous culture method of producing the product while growing microorganism. Because the fermentation tank volume is small or for other reasons, the use of multiple fermentation tanks is also possible. In this case, a high productivity of fermentation product can be obtained in a continuous culture even by plumbing multiple fermentation tanks in parallel or series.

The microorganism is not particularly limited, for example, there are listed yeasts such as baker's yeast widely used in fermentation industries, bacteria such as *Bacillus* coli and coryneform bacteria, filamentous fungi, actinomycetes and the like. The microorganism includes culture cells such as animal cell and insect cell. The microorganism used may be those isolated from natural environments, or those modified partly in property by mutation evolution or artificial recombination of genes.

EXAMPLES

Hereinafter, our methods are explained in more detail using Examples, but this disclosure is not limited to the following Examples.

Reference Example 1

Preparation of Yeast Strain Having Lactic Acid-Producing Ability

Yeast strain having a lactic acid-producing ability was established as follows. Specifically, yeast strain having an L-lactic acid-producing ability was established by coupling human-derived L-LDH gene at the downstream of PDC1 promoter on yeast genome. For polymerase chain reaction (PCR), La-Taq (manufactured by Takara Shuzo Co., Ltd.) or KOD-Plus-polymerase (manufactured by Toyobo Co., Ltd.) was used, and it was conducted according to the attachment instruction manual.

After culture recovery of human breast cancer-established cell (MCF-7), total RNA was extracted using TRIZOL Reagent (a solution of phenol and guanidine isothiocyanate manufactured by invitrogen Corporation), and using the resulting total RNA as a template, cDNA was synthesized by reverse transcription reaction using SuperScript Choice System (manufactured by Invitrogen Corporation). The detail of these operations was in accordance with each attachment protocol. The cDNA obtained was used as an amplification template of the subsequent PCR.

Using the cDNA obtained by the above-described operation as an amplification template, cloning of L-LDH gene was conducted by PCR with KOD-Plus-polymerase that oligonucleotide denoted by sequence numbers 1 and 2 was primer-set. Each PCR-amplified fragment was purified, and the terminal was phospholated with T4 Polynucleotide Kinase (manufactured by Takara Shuzo Co., Ltd.), which was then ligated to pUC118 vector (one that was cut with restricted enzyme HincII and the cut surface was subjected to dephosphorylation treatment). The ligation was conducted using DNA Ligation Kit Ver. 2 (manufactured by Takara Shuzo Co., Ltd.). *E. coli* DH5a was transformed by the ligation plasmid product, and plasmid DNA was recovered thereby to obtain a plasmid that human-derived L-LDH gene (accession number; AY009108, sequence number 3) was sub-cloned. The pUC118 plasmid inserted with the resultant L-LDH gene was digested with restricted enzymes XhoI and NotI, each DNA fragment obtained was inserted into XhoI/NotI cut site of vector pTRS11 for yeast expression. In this way, human-derived L-LDH gene expression plasmid pL-LDH5 was obtained.

Using plasmid pL-LDH5 containing human-derived L-LDH gene as an amplification template, by PCR that oligonucleotide denoted by sequence numbers 4 and 5 was primer-set, human-derived L-LDH gene of 1.3 kb and DNA fragment containing terminator sequence of *saccharomyces-cerevisia*-derived TDH3 gene were amplified. Using plasmid pRS424 as an amplification template, by PCR that oligonucleotide denoted by sequence numbers 6 and 7 was primer-set, DNA fragment containing *saccharomyces-cervisia*-derived TRP1 gene of 1.2 kb was amplified. Respective DNA fragments were separated by 1.5% agarose gel electrophoresis, and purified in accordance with the ordinary method. The mixture of the 1.3 kb fragment with the 1.2 kb fragment obtained here was used as an amplification template, the product obtained by PCR that oligonucleotide denoted by sequence numbers 4 and 7 was primer-set was treated by 1.5% agarose gel electrophoresis, and DNA fragment of 2.5 kb coupled with human-derived LDH gene and TRP1 gene was prepared in accordance with the ordinary method. By using this DNA fragment of 2.5 kb, budding yeast NBRC10505 strain was transformed into tryptophan-independence in accordance with the ordinary method.

Confirmation whether the resulting transformed cell is a cell that human-derived L-LDH gene is coupled at the downstream of PDC1 promoter on yeast genome or not was done as follows. First, genomic DNA of the transformed cell was prepared in accordance with the ordinary method, and confirmation was done by that using this as an amplification template, by PCR that oligonucleotide denoted by sequence numbers 8 and 9 was primer-set, the amplified DNA fragment of 0.7 kb was obtained. Whether the transformed cell has a lactic acid-producing ability or not was confirmed by that lactic acid was contained in culture supernatant that the transformed cell was cultured in a SC culture medium (METHODS IN YEAST GENETICS 2000 EDITION, CSHL PRESS), by measuring the amount of lactic acid by HPLC method in the following condition.

Column: Shim-Pack SPR-H (manufactured by Shimadzu Corporation), mobile phase: 5 mM p-toluenesulfonic acid (flow rate 0.8 mL/min), reaction liquid: 5 mM p-toluenesulfonic acid, 20 mM Bis-Tris, 0.1 mM EDTA×2Na (flow rate 0.8 mL/min), detection method: electric conductivity, temperature: 45° C.

Optical purity measurement of L-lactic acid was done by HPLC method in the following condition.

Column: TSK-gel Enantio L1 (manufactured by Tosoh Corporation), mobile phase: 1 mM copper sulfate aqueous solution, flow rate: 1.0 mL/min, detection method: UV254 mm, temperature: 30° C.

Optical purity of L-lactic acid was calculated by a formula 4. Here, L represents concentration of L-lactic acid, and D represents concentration of D-lactic acid.

Optical purity(%)=100×(L−D)/(L+D)  (Formula 4)

As a result of HPLC analysis, L-lactic acid of 4 g/L was detected, and D-lactic acid was below the detection limit. Based on the above review, it was confirmed that this transfectant had an L-lactic acid-producing ability. The resulting transformed cell was denoted as yeast SW-1 strain, which was used in the following Examples.

Reference Example 2

Production of L-Lactic Acid by Batch Fermentation

Most typical batch fermentation as a fermentation mode using a microorganism was conducted, and the productivity of lactic acid was evaluated. The batch fermentation test was carried out using a lactic acid fermentation medium shown in Table 1. The medium was used after high-pressure steam sterilization (121° C., 15 minutes). As the microorganism, yeast SW-1 strain established in Reference example 1 was used, regarding the evaluation on the concentration of lactic acid being a product, it was evaluated using HPLC shown in Reference example 1, for measuring glucose concentration, Glucose Test Wako C (manufactured by Wako Pure Chemical Industries, Ltd.) was used. The operating condition of Reference example 2 is shown below.

Reaction tank volume (amount of lactic acid fermentation medium): 2 (L), temperature adjustment: 30 (° C.), reaction tank airflow quantity: 0.2 (L/min), reaction tank stirring speed: 400 (rpm), pH adjustment: adjusted at pH 5 with 1N calcium hydroxide First, SW-1 strain was shake-cultured in 5 ml of lactic acid fermentation medium in a test tube overnight (prior pre-culture). A prior pre-culture solution was inoculated in 100 ml of fresh lactic acid fermentation medium, and it was shake-cultured in a Sakaguchi flask of 500 ml volume for 24 hours (pre-culture). Temperature adjustment and pH adjustment were done to carry out fermentation. The growth amount of microorganism in this case was 15 by absorbance at 600 nm. The result of batch fermentation is shown in Table 2.

TABLE 1

| Glucose | 100 g/L |
|---|---|
| Yeast Nitrogen base w/o amino acid (Difco Corporation) | 6.7 g/L |
| Standard 19 amino acids except leucine | 152 mg/L |
| Leucine | 760 mg/L |
| Inositol | 152 mg/L |

TABLE 1-continued

| p-Aminobenzoic acid | 16 mg/L |
|---|---|
| Adenine | 40 mg/L |
| Uracil | 152 mg/L |

TABLE 2

| Fermentation time | 72 hours |
|---|---|
| Glucose fed | 100 g |
| Total production amount of lactic acid | 26 g |
| Glucose unutilized | 0 g |
| Lactic acid yield to sugar | 26% |
| Production speed of lactic acid | 0.36 g/L/hr |

Reference Example 3

Permeability Evaluation of Magnesium Sulfate Through Nano-Filtration Membrane

To 10 L of pure water, 10 g of magnesium sulfate (manufactured by Wako Pure Chemical Industries, Ltd.) was added, and stirred at 25° C. for 1 hour, thereby to prepare a 1000 ppm magnesium sulfate aqueous solution. Next, 10 L of the magnesium sulfate aqueous solution prepared above was poured into a raw water tank 1 of a membrane filtration apparatus shown in FIG. 1. As a 90 φ nano-filtration membrane shown at reference number 7 of FIG. 2, crosslinked piperazine polyamide semipermeable membrane "UTC60" (nano-filtration membrane 1, manufactured by Toray Industries, Inc.), crosslinked piperazine polyamide semipermeable membrane "NF-400" (nano-filtration membrane 2, manufactured by Filmtec Corporation), polyamide semipermeable membrane "NF99" (nano-filtration membrane 3, manufactured by Alfa-Laval Corporation), and cellulose acetate semipermeable membrane "GEsepa" (nano-filtration membrane 4, manufactured by GE Osmonics Corporation) were each set to a cell made of stainless steel (SUS316), the temperature of raw water was adjusted at 25° C., and the pressure of high-pressure pump 3 was adjusted at 0.5 MPa, and a permeated liquid 4 was recovered. The concentrations of magnesium sulfate contained in the raw water tank 1 and permeated liquid 4 were analyzed by an ion chromatography (manufactured by DIONEX Corporation) in the following condition, and permeability of magnesium sulfate was calculated.

Anion: column (AS4A-SC (manufactured by DIONEX Corporation)), eluant (1.8 mM sodium carbonate/1.7 mM sodium hydrogen carbonate), temperature (35° C.)

Cation: column (CS12A (manufactured by DIONEX Corporation)), eluant (20 mM methanesulfonic acid), temperature (35° C.)

The result is shown in Table 3.

TABLE 3

| | Product name (Manufacture name) | Membrane Material | Filtration pressure (MPa) | Concentration of magnesium sulfate in raw water (ppm) | Concentration of magnesium sulfate in permeated water (ppm) | Permeability of magnesium sulfate (%) |
|---|---|---|---|---|---|---|
| Nano-filtration membrane 1 | UTC60 (Toray) | Crosslinked piperazine polyamide | 0.5 | 1000 | 2 | 0.2 |

TABLE 3-continued

| | Product name (Manufacture name) | Membrane Material | Filtration pressure (MPa) | Concentration of magnesium sulfate in raw water (ppm) | Concentration of magnesium sulfate in permeated water (ppm) | Permeability of magnesium sulfate (%) |
|---|---|---|---|---|---|---|
| Nano-filtration membrane 2 | NF-400 (Filmtec) | Crosslinked piperazine polyamide | 0.5 | 1000 | 20 | 2 |
| Nano-filtration membrane 3 | NF-99 (Alfa-Laval) | Polyamide | 0.5 | 1000 | 20 | 2 |
| Nano-filtration membrane 4 | GEsepa (GEosmonics) | Cellulose Acetate | 0.5 | 1000 | 30 | 3 |

Reference Example 4

Permeability Evaluation of Citric Acid Through Nano-Filtration Membrane

To 10 L of pure water, 10 g of citric acid (manufactured by Wako Pure Chemical Industries, Ltd.) was added, and stirred at 25° C. for 1 hour, thereby to prepare a 1000 ppm citric acid aqueous solution. Next, permeated liquids through nano-filtration membranes 1 to 4 were recovered in the same condition as Reference example 3. The concentrations of citric acid contained in the raw water tank 1 and permeated liquid 4 were analyzed by a high-performance liquid chromatography (manufactured by Shimadzu Corporation) in the following condition, and permeability of citric acid, and permeability of citric acid/permeability of magnesium sulfate were calculated.

Column: Shim-Pack SPR-H (manufactured by Shimadzu Corporation), mobile phase: 5 mM p-toluenesulfonic acid (flow rate 0.8 mL/min), reaction liquid: 5 mM p-toluenesulfonic acid, 20 mM Bis-Tris, 0.1 mM EDTA×2Na (flow rate 0.8 mL/min), detection method: electric conductivity, temperature: 45° C.

The result is shown in Table 4.

Reference Examples 5 to 25

Preparation of Culture Solution to be Filtered Through Nano-Filtration Membrane

The culture solution (2 L) subjected to lactic acid fermentation in Reference examples 1, 2 was added dropwise with concentrated sulfuric acid (Wako Pure Chemical Industries, Ltd.) till pHs became 1.9 (Reference example 5), 2.0 (Reference examples 6 to 9), 2.2 (Reference examples 10 to 13), 2.6 (Reference examples 14 to 20), and 4.0 (Reference examples 21 to 24), respectively, then stirred at 25° C. for 1 hour, thereby calcium lactate in the culture solution was changed into lactic acid and calcium sulfate. Next, calcium sulfate precipitated was subjected to suction filtration using a qualitative filter paper No. 2 (manufactured by Advantech Co., Ltd.) for the precipitate to be filtered out, and filtrate of 2 L was recovered. Also for a culture solution (2 L) of pH 5 without adding concentrated sulfuric acid, a separation experiment was conducted (Reference example 25).

(Separation Experiment by Nano-Filtration Membrane)

Figure 2:
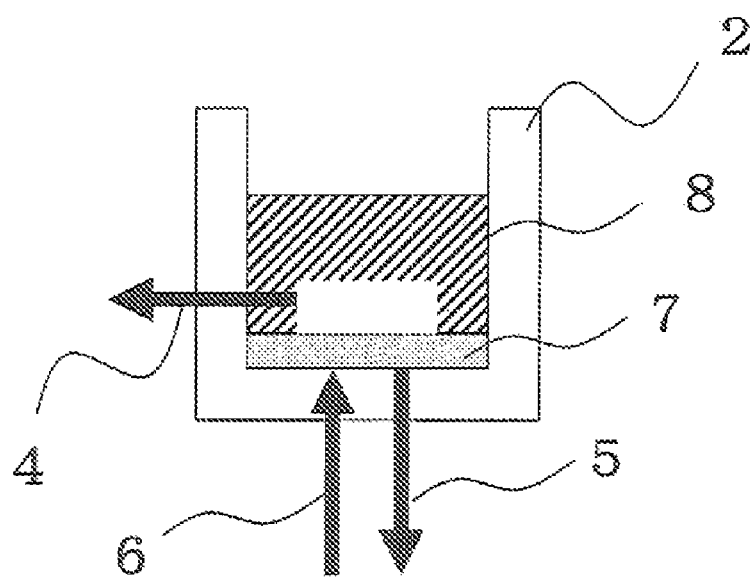
FIG. 2 is a schematic diagram showing one example of cell cross-section equipped with a nano-filtration membrane of a nano-filtration membrane separator.

Next, the filtrate of 2 L obtained in the above-described Example was poured into the raw water tank 1 of the membrane filtration apparatus shown in FIG. 1. As a 90 φ nano-filtration membrane of reference numeral 7 in FIG. 2, the

TABLE 4

| | Product name (Manufacture name) | Membrane material | Filtration pressure (MPa) | Concentration of citric acid in raw water (ppm) | Concentration of citric acid in permeated Water (ppm) | Permeability of citric acid (%) | Permeability of citric acid/ Permeability of magnesium sulfate |
|---|---|---|---|---|---|---|---|
| Nano-filtration membrane 1 | UTC60 (Toray) | Crosslinked piperazine polyamide | 0.5 | 1000 | 180 | 18 | 70 |
| Nano-filtration membrane 2 | NF-400 (Filmtec) | Crosslinked piperazine polyamide | 0.5 | 1000 | 140 | 14 | 7 |
| Nano-filtration membrane 3 | NF-99 (Alfa-Laval) | Polyamide | 0.5 | 1000 | 160 | 16 | 8 |
| Nano-filtration membrane 4 | GEsepa (GEosmonics) | Cellulose acetate | 0.5 | 1000 | 60 | 6 | 2 | above-described nano-filtration membranes 1 to 4 were each set to a cell made of stainless steel (SUS316), the pressures of high-pressure pump 3 were adjusted at 1 MPa, 3 MPa, 4 MPa and 5 MPa, respectively, and permeated liquid 4 at the respective pressures was recovered. The concentrations of sulfate ion and calcium ion contained in the raw water tank 1 and permeated liquid 4 were analyzed in the same condition as Reference example 3 by an ion chromatography (manufactured by DIONEX Corporation), and the concentration of lactic acid was analyzed in the same condition as Reference example 1 by a high-performance liquid chromatography (manufactured by Shimadzu Corporation). The result is shown in Table 5.

Examples 1 to 4

Concentration of Lactic Acid-Containing Solution and Distillation of Concentrated Liquid Using Evaporator Water was evaporated for concentrating 1 L each of permeated liquids of Reference examples 7, 11, 15 and 22 under reduced pressure (50 hPa) using a rotary evaporator (manufactured by Tokyo Rikakikai Co., Ltd.). In this time, no deposition of calcium sulfate was observed.

TABLE 5

|  | Nano-filtration membrane | pH | Filtration pressure (MPa) | Membrane permeation flux (m³/m²/day) | Calcium ion concentration | | | Sulfate ion concentration | | | Lactic acid concentration | | |
| --- | --- | --- | --- | --- | --- | --- | --- | --- | --- | --- | --- | --- | --- |
|  |  |  |  |  | Raw water (mg/L) | Permeated liquid (mg/L) | Removal rate (%) | Raw water (mg/L) | Permeated liquid (mg/L) | Removal rate (%) | Raw water (g/L) | Permeated liquid (g/L) | Permeability (%) |
| Reference example 5 | Nano-filtration membrane 1 | 1.9 | 4 | 2.54 | 557 | 0.8 | 99.9 | 1678 | 428 | 74.5 | 45 | 22.9 | 50.9 |
| Reference example 6 | Nano-filtration membrane 1 | 2 | 1 | 1.01 | 543 | 1 | 99.8 | 1651 | 418.2 | 74.7 | 45 | 25.2 | 56.0 |
| Reference example 7 | Nano-filtration membrane 1 | 2 | 3 | 1.89 | 549 | 1 | 99.8 | 1654 | 433 | 73.8 | 44 | 24.1 | 54.8 |
| Reference example 8 | Nano-filtration membrane 1 | 2 | 4 | 2.54 | 557 | 0.8 | 99.9 | 1678 | 428.3 | 74.5 | 45 | 22.9 | 50.9 |
| Reference example 9 | Nano-filtration membrane 1 | 2 | 5 | 2.95 | 574 | 0.9 | 99.8 | 1712 | 418.7 | 75.5 | 46 | 21.8 | 47.4 |
| Reference example 10 | Nano-filtration membrane 1 | 2.2 | 1 | 1 | 812 | 0.6 | 99.9 | 1181 | 134 | 88.7 | 45 | 26 | 57.8 |
| Reference example 11 | Nano-filtration membrane 1 | 2.2 | 3 | 1.88 | 813 | 0.7 | 99.9 | 1162 | 135 | 88.4 | 44 | 24.9 | 56.6 |
| Reference example 12 | Nano-filtration membrane 1 | 2.2 | 4 | 2.5 | 811 | 0.8 | 99.9 | 1165 | 133 | 88.6 | 48 | 24.5 | 51.0 |
| Reference example 13 | Nano-filtration membrane 1 | 2.2 | 5 | 2.98 | 821 | 1 | 99.9 | 1160 | 129 | 88.9 | 48 | 23.8 | 49.6 |
| Reference example 14 | Nano-filtration membrane 1 | 2.6 | 1 | 1.02 | 1493 | 1.5 | 99.9 | 920 | 28 | 97.0 | 49 | 27.1 | 55.3 |
| Reference example 15 | Nano-filtration membrane 1 | 2.6 | 3 | 1.9 | 1498 | 1.3 | 99.9 | 919 | 28 | 97.0 | 48 | 26.8 | 55.8 |
| Reference example 16 | Nano-filtration membrane 1 | 2.6 | 4 | 2.5 | 1497 | 1.3 | 99.9 | 918 | 24 | 97.4 | 48 | 24.9 | 51.9 |
| Reference example 17 | Nano-filtration membrane 1 | 2.6 | 5 | 2.92 | 1501 | 1.2 | 99.9 | 909 | 21 | 97.7 | 47 | 24 | 51.1 |
| Reference example 18 | Nano-filtration membrane 2 | 2.6 | 4 | 2.12 | 1497 | 4.8 | 99.7 | 918 | 26.8 | 97.1 | 48 | 21.2 | 44.2 |
| Reference example 19 | Nano-filtration membrane 3 | 2.6 | 4 | 2.08 | 1497 | 6.7 | 99.6 | 918 | 24.3 | 97.4 | 48 | 21.9 | 45.6 |
| Reference example 20 | Nano-filtration membrane 4 | 2.6 | 4 | 1.48 | 1497 | 2.1 | 99.9 | 918 | 1.8 | 99.8 | 48 | 21 | 43.8 |
| Reference example 21 | Nano-filtration membrane 1 | 4 | 1 | 1.01 | 4921 | 3.1 | 99.9 | 391 | 8.5 | 97.8 | 48 | 21.2 | 44.2 |
| Reference example 22 | Nano-filtration membrane 1 | 4 | 3 | 1.9 | 4919 | 3 | 99.9 | 401 | 8.1 | 98.0 | 48 | 21 | 43.8 |
| Reference example 23 | Nano-filtration membrane 1 | 4 | 4 | 2.51 | 4909 | 2.9 | 99.9 | 402 | 7.9 | 98.0 | 49 | 20.9 | 42.7 |
| Reference example 24 | Nano-filtration membrane 1 | 4 | 5 | 2.95 | 4918 | 2.5 | 99.9 | 410 | 7.7 | 98.1 | 49 | 20.9 | 42.7 |
| Reference example 25 | Nano-filtration membrane 1 | 5 | 1 | 0.44 | 5321 | 3.8 | 99.9 | — | — | — | 20 | 8.3 | 41.5 |

As shown in Table 5, it was known that calcium sulfate was removed at all pHs and filtration pressures in a high efficiency. In the above-described Reference examples 5 to 25, calcium sulfate was removed in a high efficiency at the above-described filtration pressures not changing a new membrane for the nano-filtration membrane.

Next, vacuum distillation was conducted at 133 Pa and 130° C. In order to confirm racemization of lactic acid distilled, optical purity before and after distillation was measured by a high-performance liquid chromatography to find no deterioration of optical purity. The result is shown in Table 6.

TABLE 6

| | Nano-filtration membrane | pH | Lactic acid concentration of permeated liquid through nano-filtration membrane (g/L) | Lactic acid concentration after concentration by evaporator (g/L) | Deposit after concentration | Optical purity before distillation (% e.e.) | Optical purity after distillation (% e.e.) | Distillation yield (%) |
|---|---|---|---|---|---|---|---|---|
| Example 1 | Nano-filtration membrane 1 | 2 | 24.1 | 810 | None | 99.9 | 99.9 | 81 |
| Example 2 | Nano-filtration membrane 1 | 2.2 | 24.9 | 798 | None | 99.9 | 99.9 | 84 |
| Example 3 | Nano-filtration membrane 1 | 2.6 | 26.8 | 821 | None | 99.9 | 99.9 | 88 |
| Example 4 | Nano-filtration membrane 1 | 4 | 21 | 788 | None | 99.9 | 99.9 | 92 |

Examples 5 to 13

Concentration of Lactic Acid-Containing Solution Using Reverse Osmosis Membrane)

1.9 L each of permeated liquids of Reference example 5 (nano-filtration membrane 1, pH 1.9), Reference example 7 (nano-filtration membrane 1, pH 2.0), Reference example 11 (nano-filtration membrane 1, pH 2.2), Reference example 15 (nano-filtration membrane 1, pH 2.6), Reference example 18 (nano-filtration membrane 2, pH 2.6), Reference example 19 (nano-filtration membrane 3, pH 2.6), Reference example 20 (nano-filtration membrane 4, pH 2.6), Reference example 22 (nano-filtration membrane 1, pH 4.0) and Reference example 25 (nano-filtration membrane 1, pH 5.0) was poured into the raw water tank 1 of the membrane filtration apparatus shown in FIG. 1. As a 90 φ reverse osmosis membrane of reference numeral 7 in FIG. 2, reverse osmosis membranes of polyamide (UTC-70, manufactured by Toray Industries, Inc.) were each set to a cell made of stainless steel (SUS316), the pressures of high-pressure pump 3 were adjusted at 3 MPa respectively, and reverse osmosis membrane-concentrated liquid 5 was recovered. The concentration of lactic acid contained in the membrane-concentrated liquid was analyzed in the same condition as Reference example 1 by a high-performance liquid chromatography (manufactured by Shimadzu Corporation). The result is shown in Table 7.

(Distillation of Lactic Acid-Containing Solution)

Water was evaporated for concentrating 0.4 L each of the above-described reverse osmosis membrane-concentrated liquids under reduced pressure (50 hPa) using a rotary evaporator (manufactured by Tokyo Rikakikai Co., Ltd.). In this time, no deposition of calcium sulfate was observed. Next, vacuum distillation was conducted at 133 Pa and 130° C. In order to confirm racemization of lactic acid distilled, optical purity before and after distillation was measured by a high-performance liquid chromatography to find no deterioration of optical purity. The result is shown in Table 7.

TABLE 7

| | Nano-filtration membrane | pH | Lactic acid concentration of permeated liquid through nano-filtration membrane (g/L) | Operation pressure (MPa) | Lactic acid concentration of concentrated liquid through reverse osmosis membrane (g/L) | Deposition after concentration | Optical purity before distillation (% e.e.) | Optical purity after distillation (% e.e.) | Distillation yield (%) |
|---|---|---|---|---|---|---|---|---|---|
| Example 5 | Nano-filtration membrane 1 | 1.9 | 22.9 | 3 | 114.5 | None | 99.9 | 99.9 | 76 |
| Example 6 | Nano-filtration membrane 1 | 2 | 24.1 | 3 | 120.5 | None | 99.9 | 99.9 | 81 |
| Example 7 | Nano-filtration membrane 1 | 2.2 | 24.9 | 3 | 124.5 | None | 99.9 | 99.9 | 84 |
| Example 8 | Nano-filtration membrane 1 | 2.6 | 26.8 | 3 | 134 | None | 99.9 | 99.9 | 88 |
| Example 9 | Nano-filtration membrane 2 | 2.6 | 21.2 | 3 | 106 | None | 99.9 | 99.9 | 80 |
| Example 10 | Nano-filtration membrane 3 | 2.6 | 21.9 | 3 | 109.5 | None | 99.9 | 99.9 | 80 |
| Example 11 | Nano-filtration membrane 4 | 2.6 | 21 | 3 | 105 | None | 99.9 | 99.9 | 84 |

TABLE 7-continued

| | Nano-filtration membrane | pH | Lactic acid concentration of permeated liquid through nano-filtration membrane (g/L) | Operation pressure (MPa) | Lactic acid concentration of concentrated liquid through reverse osmosis membrane (g/L) | Deposition after concentration | Optical purity before distillation (% e.e.) | Optical purity after distillation (% e.e.) | Distillation yield (%) |
|---|---|---|---|---|---|---|---|---|---|
| Example 12 | Nano-filtration membrane 1 | 4 | 21 | 3 | 105 | None | 99.9 | 99.9 | 92 |
| Example 13 | Nano-filtration membrane 1 | 5 | 8.3 | 3 | 41.5 | None | 99.9 | 99.9 | 90 |

Comparative Example 1

Filtration Experiment by Qualitative Filer Paper

In the same manner as Examples 1 to 4, the culture solution (2 L) subjected to lactic acid fermentation in Reference examples 1, 2 was added dropwise with concentrated sulfuric acid (Wako Pure Chemical Industries, Ltd.) till pH became 2.0, then stirred at 25° C. for 1 hour. Calcium sulfate precipitated was filtered out by suction filtration using a qualitative filter paper No. 2 (manufactured by Advantech Co., Ltd.). The concentration of calcium sulfate contained in the filtrate was analyzed by an ion chromatography to find a calcium ion concentration of 549 mg/L. From which, it was known that calcium sulfate was not sufficiently removed.

Comparative Example 2

Distillation of Lactic Acid

Water was evaporated for concentrating 1 L of the filtrate (lactic acid concentration: 24 g/L) obtained in Comparative example 1 under reduced pressure (50 hPa) using a rotary evaporator (manufactured by Tokyo Rikakikai Co., Ltd.), and calcium sulfate which was not removed by the above-described qualitative filter paper was deposited. Next, vacuum distillation was conducted at 133 Pa and 130° C. In order to confirm racemization of lactic acid distilled, optical purity of lactic acid before and after distillation was measured in the same condition as Reference example 1 by a high-performance liquid chromatography to find the deterioration of optical purity. In the distillation residue, partly oligomerized lactic acid was confirmed. The result is shown in Table 8.

TABLE 8

| Optical purity before distillation (% e.e.) | Optical purity after distillation (% e.e.) |
|---|---|
| 99 | 94 |

From the foregoing Examples and Comparative examples, it became clear that calcium sulfate in a culture solution can be removed in a high efficiency by a nano-filtration membrane. Namely, according to the present invention, calcium component in a lactic acid solution in a microorganism culture solution can be removed in a high efficiency by a nano-filtration membrane, and it became clear that the calcium component is not deposited even by concentration, further, racemization and oligomerization does not proceed even when a distillation step is applied.

INDUSTRIAL APPLICABILITY

Lactic acid obtained by the method of producing lactic acid is suitable for monomer raw material of biodegradable plastic polylactic acid, as well as food and medicine.

The invention claimed is:

1. A method of producing lactic acid comprising the steps of:
   (a) producing lactic acid in a first culture solution by microbial fermentation, wherein a calcium salt is added to the first culture solution to maintain a selected pH during the microbial fermentation and then removing the resulting calcium component in said first culture solution as a poorly-soluble sulfate salt to obtain a second culture solution;
   (b) filtering the second culture solution through a nano-filtration membrane to obtain a first filtered culture solution;
   (c) filtering the first filtered culture solution through a reverse osmosis membrane to obtain a second filtered culture solution, thereby increasing the concentration of lactic acid in the second filtered culture solution; and
   (d) distilling the second filtered culture solution under a pressure of 1 Pa to atmospheric pressure at a temperature of 25° C. to 200° C. to recover substantially optically pure lactic acid.

2. The method of claim 1, wherein the pH of the first culture solution in step (a) is not less than 2 and not more than 4.5.

3. The method of claim 1, wherein a ratio of permeability of magnesium sulfate to permeability of citric acid through said nano-filtration membrane is 3 or more at 0.5 MPa of operation pressure, 25° C. of liquid temperature, and 1000 ppm of magnesium sulfate concentration.

4. The method of claim 1, wherein a permeability of magnesium sulfate through said nano-filtration membrane is 1.5% or less at 0.5 MPa of operation pressure, 25° C. of liquid temperature, and 1000 ppm of magnesium sulfate concentration.

5. The method of claim 1, wherein a membrane material of said nano-filtration membrane includes a polyamide.

6. The method of claim 5, wherein said polyamide is composed of crosslinked piperazine polyamide as a main component, and contains a constitutional component shown in formula (1),

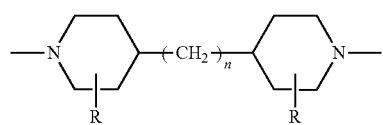
(1)
wherein R represents —H or —CH$_3$, and n represents an integer from 0 to 3, inclusive.
7. The method of claim 1, wherein filtration pressure of the second culture solution in step (b) is not less than 0.1 MPa and not more than 8 MPa.
* * * * *

UNITED STATES PATENT AND TRADEMARK OFFICE
CERTIFICATE OF CORRECTION

PATENT NO. : 8,349,597 B2  
APPLICATION NO. : 12/666690  
DATED : January 8, 2013  
INVENTOR(S) : Ito et al.

Page 1 of 1

It is certified that error appears in the above-identified patent and that said Letters Patent is hereby corrected as shown below:

In the Claims

In Column 27

Before Formula 1, please insert -- STR (I) --.

Signed and Sealed this  
Eleventh Day of June, 2013

Teresa Stanek Rea  
*Acting Director of the United States Patent and Trademark Office*